United States Patent [19]
Larsson et al.

[11] Patent Number: 5,965,061
[45] Date of Patent: Oct. 12, 1999

[54] METHOD OF INCREASING THE SHELF LIFE OF A COLORIMETRIC DEVICE FOR INDICATING CARBON DIOXIDE AND PACKAGE CONTAINING SUCH DEVICE

[75] Inventors: Anders Larsson, Bromma; Gunilla Östberg, Vallentuna; Paul Krill, Järfälla; Andras Gedeon, Täby, all of Sweden

[73] Assignee: ICOR AB, Bromma, Sweden

[21] Appl. No.: 08/594,059

[22] Filed: Jan. 30, 1996

[30] Foreign Application Priority Data

Feb. 3, 1995 [SE] Sweden .................................. 9500401

[51] Int. Cl.$^6$ ................. G01N 31/22; G01J 1/48
[52] U.S. Cl. ............... 252/408.1; 422/86; 426/442
[58] Field of Search .................... 252/408.1; 422/56, 422/61, 87, 86; 428/69, 305.5; 128/207.14; 206/6, 305; 95/139; 423/220; 426/442; 436/164, 183

[56] References Cited

U.S. PATENT DOCUMENTS

| | | | |
|---|---|---|---|
| 4,038,148 | 7/1977 | Miler et al. | 195/127 |
| 4,278,499 | 7/1981 | Abramson et al. | |
| 4,728,499 | 3/1988 | Fehder | 422/56 |
| 4,904,449 | 2/1990 | Heckmann | 422/87 |
| 4,946,649 | 8/1990 | Pannwitz | 422/60 |
| 5,005,572 | 4/1991 | Raemer et al. | |
| 5,035,860 | 7/1991 | Kleingeld et al. | 422/61 |
| 5,291,879 | 3/1994 | Babb et al. | 128/200.26 |
| 5,375,592 | 12/1994 | Kirk et al. | 128/207.14 |
| 5,407,829 | 4/1995 | Wolfbeis et al. | 436/1 |
| 5,439,648 | 8/1995 | Balderson et al. | 422/86 |
| 5,472,668 | 12/1995 | Mills et al. | 422/56 |

FOREIGN PATENT DOCUMENTS

| | | |
|---|---|---|
| 919510 | 2/1953 | Germany . |
| 1 007 525 | 8/1955 | Germany . |
| WO91/05252 | 4/1991 | WIPO . |

OTHER PUBLICATIONS

"Equilibrium Studies on Colorimetric Plastic Film Sensors for Carbon Dioxide" in Analytical Chemistry, vol. 64, p. 1383 (1992).

Smolander, M et al., Leak Indicators For Modified Gas Atmosphere Packages, Trends Food Sci. & Technol. (1997), 8 (4), pp. 101–106.

*Primary Examiner*—Shean C. Wu
*Attorney, Agent, or Firm*—McDermott, Will & Emery

[57] ABSTRACT

A method of increasing the shelf life of a reversible calorimetric device for indicating carbon dioxide is disclosed, which method comprises placing said device together with at least one non-toxic pH-lowering gas in a gas-tight wrapping or casing. A package is also disclosed which is prepared by means of said method. The invention also relates to the use of a non-toxic pH-lowering gas for increasing the shelf life of a device of the above mentioned type.

4 Claims, 2 Drawing Sheets

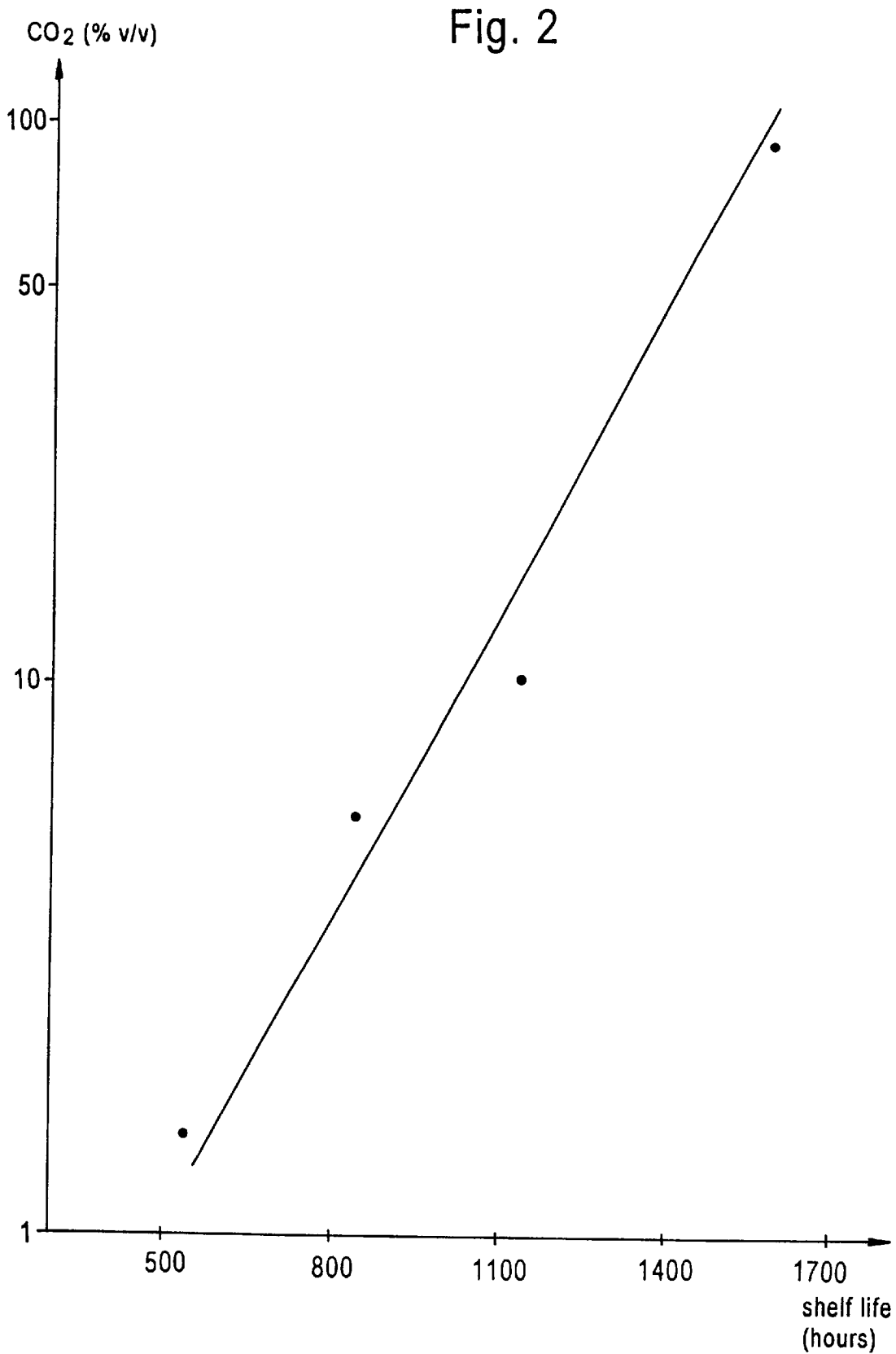

METHOD OF INCREASING THE SHELF LIFE OF A COLORIMETRIC DEVICE FOR INDICATING CARBON DIOXIDE AND PACKAGE CONTAINING SUCH DEVICE

TECHNICAL FIELD

The present invention relates to a method of increasing the shelf life of a calorimetric device for indicating carbon dioxide and to a package with increased shelf life containing such calorimetric device. The invention also relates to the new use of a non-toxic pH-lowering gas for increasing the shelf life of a colorimetric device for indicating carbon dioxide.

TECHNICAL BACKGROUND

Methods for the detecting or measuring the content of gaseous carbon dioxide ($CO_2$) in a mixture of gases utilizing chemical absorption belongs to the well-known technique.

German Patents Nos 919510 and 1 007 525 both discloses selective absorption of $CO_2$ on a substance which contains a pH-sensitive dye. The change in the pH-value caused by the $CO_2$ bound to the substance becomes apparent as a change in colour of the dye which is present in the substance. Accordingly the change in colour becomes a measure of the content of $CO_2$ in the gas flow under investigation.

The problems encountered with these early systems are that the absorbing surface must be kept in hermetically closed glass tubes and that, once said surface gets into contact with the gas flow, an irreversible reaction is obtained, i.e. the device becomes unusable after having been exposed to the test gas. Thus it cannot be used e.g. for monitoring $CO_2$ concentrations which vary with time.

A reverible $CO_2$ indicator device is disclosed in U.S. Pat. No. 4,728,499. This prior art device comprises a system consisting of a pH-sensitive indicator dye, a basic substance and a viscous hygroscopic liquid. The indicator is able both to absorb and desorb $CO_2$ with a time constant of a few seconds so that it can be used e.g. in hospitals for monitoring the breathing of a patient. During exhalation, which takes about 4 seconds, the air contains 3–5 % by volume of $CO_2$ whereas the $CO_2$ content during inhalation, which typically takes about 2 seconds, is about 0.05% by volume corresponding to the normal concentration of $CO_2$ in atmospheric air. The indicator hence changes colour to and fro with breathing about 10 times a minute.

The main disadvantage of this known system is that it is strongly hygroscopic and hence the indicator will absorb water vapour from the gas under investigation ultimately resulting in that the system ceases to respond to $CO_2$. In view of the fact that exhaled air is saturated with water vapour at about 30° C. this indicator will only be able to monitor the breathing of a patient for a few minutes.

Another disadvantage exhibited by this prior art device is that the indicator must be stored in a hermetically closed, absolutely dry environment free from carbon dioxide prior to use.

Another type of a reversible calorimetric device is disclosed by U.S. Pat. No. 5,005,572 and WO91/05252 and an article in Analytical Chemistry, Vol 64, page 1383 (1992).

These systems are based on pH-sensitive indicator dyes, water-insoluble organic quarternary (e.g. ammonium or phosphonium) hydroxides as a basic substance and additional substances in order to facilitate the absorption/desorption of $CO_2$.

These known indicator devices appear to function reversibly for several days and they are indicating satisfactory both in humid and dry environments.

The major disadvantage of these devices is that the strong base decomposes with time so that the indicator slowly becomes permanently "acid" and accordingly useless. Then it exhibits the "acid" colour all the time as if it were exposed to a constantly high concentration of $CO_2$.

This decomposition of the base is strongly depending on the temperature of the environment and hence the useful length of life of an indicator device which has been stored while awaiting use is difficult to predict and check.

It is an object of the present invention to provide a method of increasing the shelf life of a reversible calorimetric device for indicating carbon dioxide.

It is another object of the present invention to provide a package of a reversible colorimetric device having increased shelf life.

THE INVENTION

According to the present invention it was surprisingly found that the shelf life of a reversible colorimetric device can be increased by storing it in a pH-lowering gas such as carbon dioxide.

Based on the finding mentioned above the invention provides as one aspect thereof a method of increasing the shelf life of a reversible colorimetric device for indicating carbon dioxide, which method comprises placing said device together with at least one non-toxic pH-lowering gas in a gas-tight wrapping or casing.

According to a preferred embodiment of the method according to the invention the pH-lowering gas contains carbon dioxide in a concentration exceeding that of normal air, suitably being at least 0.2%, preferably at least 0.3%, most preferably at least 1% and especially at least 10% by volume, the remainder to 100% suitably being air, which may contain a minor amount of water vapour.

According to another aspect of the invention there is provided a package comprising a gas-tight wrapping or casing and enclosed therein a reversible calorimetric device for indicating carbon dioxide and at least one non-toxic pH-lowering gas.

According to a preferred embodiment of the package according to the invention the pH-lowering gas contains carbon dioxide in concentrations as set forth in connection with the preferred embodiment of the method according to the invention above.

According to a further aspect of the invention there is provided the new use of a non-toxic pH-lowering gas for increasing the shelf life of a reversible calorimetric device for indicating carbon dioxide.

According to a preferred embodiment of the use according to the invention the pH-lowering gas contains carbon dioxide in concentrations as set forth in connection with the preferred embodiment of the method according to the invention above.

The reversible calorimetric device for indicating carbon dioxide the shelf life of which should be increased according to the invention may be any prior art device according to the references U.S. Pat. No. 5 005 572, WO91/05252 and Analytical Chemistry, Vol 64, page 1383 (1992) cited above which device is composed of a basic substance, a pH-sensitive dye and a substance facilitating the absorption/desorption of $CO_2$.

BRIEF DESCRIPTION OF THE DRAWING

FIG. 2 is a graph showing the shelf life at 25° C. as a function of the concentration of $CO_2$ in the surrounding air.

DETAILED DESCRIPTION OF THE INVENTION

Figure 1:
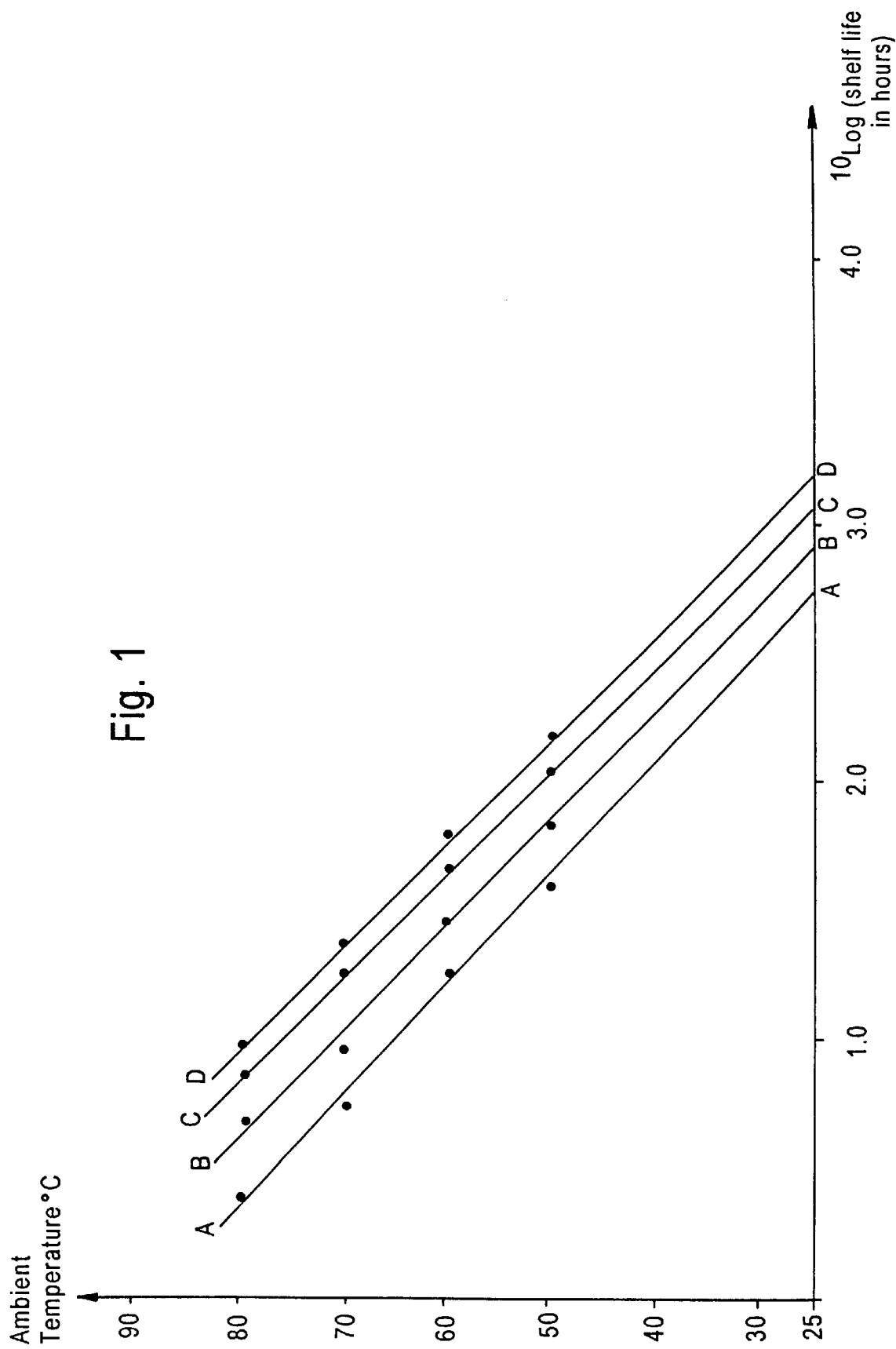
FIG. 1 is a graph showing the shelf life of a reversible colorimetric device as a function of temperature at different concentrations of carbon dioxide ($CO_2$) in the surrounding air.

For the experiments the results of which are forming the basis of FIGS. 1 and 2 a conventional reversible calorimetric device comprising a mixture of tetraoctyl-ammonium hydroxide as a base, thymol blue as the dye and tributyl phosphate applied on paper used as a carrier was used. The calorimetric device was enclosed in a gas-tight casing in an atmosphere of air containing $CO_2$ and having a relative humidity of about 50% normal ambient air containing 0.15% by volume of $CO_2$ being used as a control.

In a first series of experiments the shelf life of the calorimetric device at different ambient temperatures was measured (control: 0.15% by volume of $CO_2$). The shelf life was defined as the time required for the indicator (without being in contact with $CO_2$) to become aged to such an extent that the "basic" colour is changed in the direction to the "acid" colour corresponding to an exposure to about 1% by volume of $CO_2$.

The experiment was repeated at different concentrations of $CO_2$ in the air surrounding the indicator in the gas-tight casing.

The $^{10}$log for the shelf life in hours was plotted along the abscissa against ambient temperature in ° C. (ordinate).

From FIG. 1 the following shelf lives at 25° C. were calculated:

| $CO_2$ % v/v | Curve | Shelf life h |
|---|---|---|
| 0.15 | A | 540 |
| 5.7 | B | 830 |
| 10 | C | 1150 |
| 90 | D | 1600 |

In a further series of experiments the shelf life of a calorimetric device of the same type as that used in the experiments mentioned above was measured at 25° C. at different concentrations of $CO_2$ in the surrounding atmosphere (relative humidity 50% v/v).

The shelf life in hours was plotted along the abscissa against the concentration of $CO_2$ (% by volume) in a $^{10}$log scale (ordinate) in FIG. 2.

From FIG. 2 it can be concluded that storing the colorimetric device in the presence of $CO_2$ increases the shelf life at 25° C. with a factor about 4.

We claim:

1. A package comprising a gas-tight wrapping or casing and enclosed therein a reversible calorimetric device for indicating carbon dioxide and a gas mixture comprising A) carbon dioxide and air or B) carbon dioxide, air, and a minor amount of water vapor, the concentration of carbon dioxide of said gas mixture being at least 0.2% by volume.

2. A package according to claim 1, wherein the concentration of carbon dioxide of said gas mixture is at least 0.3% by volume.

3. A package according to claim 1, wherein the concentration of carbon dioxide of said gas mixture is at least 1% by volume.

4. A package according to claim 1, wherein the concentration of carbon dioxide of said gas mixture is at least 10% by volume.

* * * * *